(12) United States Patent
Fridie

(10) Patent No.: US 10,426,665 B1
(45) Date of Patent: Oct. 1, 2019

(54) SELF-CLEANING SYSTEM FOR VISION PROTECTIVE LENS

(71) Applicant: Ly John Fridie, Odenton, MD (US)

(72) Inventor: Ly John Fridie, Odenton, MD (US)

(\*) Notice: Subject to any disclaimer, the term of this patent is extended or adjusted under 35 U.S.C. 154(b) by 612 days.

(21) Appl. No.: 15/159,204

(22) Filed: May 19, 2016

Related U.S. Application Data

(60) Provisional application No. 62/163,504, filed on May 19, 2015.

(51) Int. Cl.
*A61F 9/02* (2006.01)
*A61F 9/06* (2006.01)
*G02C 13/00* (2006.01)

(52) U.S. Cl.
CPC ............... *A61F 9/029* (2013.01); *A61F 9/02* (2013.01); *A61F 9/061* (2013.01); *G02C 13/006* (2013.01); *G02C 13/008* (2013.01)

(58) Field of Classification Search
CPC . A61F 9/029; A61F 9/061; A61F 9/02; G02C 13/006; G02C 13/008
USPC ................................ 2/15, 426, 427, 431, 438
See application file for complete search history.

(56) References Cited

U.S. PATENT DOCUMENTS

| | | | | | |
|---|---|---|---|---|---|
| 1,839,175 | A | * | 12/1931 | Hueber | B60S 1/0413 15/250.27 |
| 2,329,757 | A | * | 9/1943 | Greenfield | G02C 11/08 15/214 |
| 2,565,362 | A | * | 8/1951 | Eloranta | G02C 7/12 2/432 |
| 2,721,352 | A | * | 10/1955 | Oishei | B60S 1/0896 15/250.12 |
| 2,888,703 | A | * | 6/1959 | Karwowska | G02C 11/08 15/250.27 |
| 3,754,298 | A | * | 8/1973 | Menil | A63H 37/00 15/250.3 |
| 4,027,354 | A | * | 6/1977 | Burpee | A42B 3/26 15/250.3 |
| 4,789,233 | A | * | 12/1988 | Arsenault | G02C 11/08 15/250.04 |
| 5,210,552 | A | * | 5/1993 | Baran | G02C 7/12 351/44 |
| 6,073,296 | A | * | 6/2000 | Bouguerfa | A42B 3/26 15/102 |
| 6,386,702 | B1 | * | 5/2002 | Maloncon | G02C 7/12 351/158 |

(Continued)

*Primary Examiner* — Alissa J Tompkins
*Assistant Examiner* — Cameron A Carter
(74) *Attorney, Agent, or Firm* — Rosenberg, Klein & Lee

(57) ABSTRACT

A self-cleaning system for a vision protective lens comprises a chassis configured to be worn on a user's head, the chassis having a main body portion defining a field of view. At least one lens is coupled in angularly displaceable manner to the chassis and disposed to extend at least partially across the field of view. At least one wiper blade unit is supported on the chassis to extend across an outer surface of the lens about the field of view. The wiper blade unit includes a blade portion engaging the outer surface of the lens. A drive portion is coupled to selectively drive angular displacement of the lens. The lens is angularly displaced in selectively driven manner relative to the wiper blade unit; and, the lens is at least partially wiped by the blade portion to be cleared prior to advancement angularly into the field of view.

17 Claims, 14 Drawing Sheets

(56) References Cited

U.S. PATENT DOCUMENTS

| | | | | |
|---|---|---|---|---|
| 6,640,379 B1* | 11/2003 | Scribner | ............... | G02C 11/08 |
| | | | | 15/250.27 |
| 6,722,766 B1* | 4/2004 | Myette | ............... | G02C 11/08 |
| | | | | 351/158 |
| 7,364,289 B1* | 4/2008 | Herring | ............... | A61F 9/029 |
| | | | | 15/250.001 |
| 8,209,783 B1* | 7/2012 | Lone Eagle | ............ | A42B 3/26 |
| | | | | 15/250.001 |
| 2010/0095439 A1* | 4/2010 | Nolan | ............... | A42B 3/24 |
| | | | | 2/421 |
| 2014/0117701 A1* | 5/2014 | Davis | ............... | A42B 3/26 |
| | | | | 296/96.15 |

* cited by examiner

SELF-CLEANING SYSTEM FOR VISION PROTECTIVE LENS

RELATED APPLICATION DATA

This Application is based on Provisional Patent Application No. 62/163,504, filed 19 May 2015.

BACKGROUND OF THE INVENTION

The present invention is generally directed to a system providing automated measures for maintaining safe visibility for lens surfaces of various vision protective devices. More specifically, the present invention is directed to a system having sufficient measures for automatically removing liquid, mud, dirt, or other such vision obstructing debris from protective lens surfaces of various vision protective devices like goggles eyewear, face shields, or the like. The system enables substantially hands free operation to clear the lens surface(s) as needed to maintain ample visibility therethrough. Safe visibility may be preserved thereby, even while the user is operating a vehicle, handling a tool, or carrying on other activities requiring active hands on control.

Most conventional devices providing vision protective lenses have like goggles, face shields, or other eye/face protective wear are provided without measures for active clearing when hit by water, dirt, or other vision impairing debris. A wearer is typically expected to manually 'wipe' off the obstructive debris and proceed. In many applications, however, the wearer's hands and attention are focused on a certain task which makes it difficult and impracticable for him/her to carry out such manual clearing action. Examples include a motorcyclist riding through rain in traffic, or negotiating turns and bumps on a dirty or muddy trail. They include among many others a technician operating a high powered tool or machinery requiring the strength and dexterity of both hands to keep the tool/machinery properly working. In such applications, it may be quite unsafe for the wearer to free a hand even for a moment to take even a quick clearing swipe to try and clear the obstruction. Typically, a wearer has no safe alternative except to stop what he/she is doing, clean the protective wear, then resume.

Even if the wearer were to manage a clearing action without undue hazard, it is often with ineffective and momentarily helpful results. Absent a drastic change in conditions, the cause of the initial obstruction (falling rain, ongoing travel through a given trail, . . . ) may linger for some time, and the clearing action may need to be repeated over and over again to be of any meaningful effect. Yet, to repeat the clearing action may raise the potential hazard to untenable levels.

There is therefore a need for a system for substantially hands free clearing of a vision protective lens of a device worn by a user. There is need for such system that simply yet effectively removes liquid and/or solid debris from the vision protective lens surface so that the wearer's field of view therethrough is adequately preserved.

SUMMARY OF THE INVENTION

It is an object of the present invention to provide a system for substantially hands free clearing of a vision protective lens of a device worn by a user.

It is another object of the present invention to provide a system that simply yet effectively removes liquid and/or solid debris from a vision protective lens surface.

It yet another object of the present invention to provide a system that provides automated hands free clearing of a vision protective lens surface worn by the user in a mariner that substantially preserves the user's field of view.

These and other objects are attained in a self-cleaning system for a vision protective lens comprising a chassis configured to be worn on a user's head, the chassis having a main body portion defining a field of view. At least one lens is coupled in angularly displaceable manner to the chassis, which lens is disposed to extend at least partially across the field of view. At least one wiper blade unit is supported on the chassis to extend across an outer surface of the lens adjacent the field of view. The wiper blade unit includes a blade portion engaging the outer surface of the lens. A drive portion is coupled to selectively drive angular displacement of the lens. The lens is angularly displaced in selectively driven manner relative to the wiper blade unit; and, the outer surface of the lens is at least partially wiped by the blade portion of the wiper unit to be cleared prior to advancement angularly into the field of view.

In certain embodiments, a self-cleaning system for a vision protective lens is provided, comprising a chassis configured to be worn on a user's head, the chassis having a main body portion defining a field of view. At least one slew ring bearing is coupled to the main body of the chassis, the slew ring bearing including a movable bearing portion coupled in angularly displaceable manner to a stationary bearing portion. At least one lens is coupled to the movable portion of the slew ring bearing for angular displacement therewith. The lens is supported by the movable portion to extend at least partially across the field of view. At least one wiper blade unit is fixedly supported on the chassis to extend in inclined manner across an outer surface of the lens adjacent the field of view. The wiper blade unit includes a protective shell portion and a blade portion emerging therefrom to engage the outer surface of the lens. A drive portion coupled to the chassis engages the slew ring bearing to selectively drive angular displacement of the movable portion thereof. The lens is thereby angularly displaced in selectively driven manner relative to the wiper blade unit; and, the outer surface of the lens is at least partially wiped by the blade portion of the wiper unit to be cleared prior to advancement angularly into the field of view.

In certain other embodiments, a self-cleaning system for a vision protective lens is integrated in a goggle device, comprising a chassis configured to be worn on a user's head, the chassis having a main body portion defining fields of view for right and left lens openings. A pair of slew ring bearings are coupled to the main body of the chassis respectively at the right and left openings, each slew ring bearing including a movable bearing portion coupled in angularly displaceable manner to a stationary bearing portion. A pair of lenses are each coupled to the movable portion of one slew ring bearing for angular displacement therewith, the lenses being supported by the movable portions to extend over the right and left lens openings and thereby extend at least partially across the respective fields of view. A pair of wiper blade units are each fixedly supported on the chassis to extend in inclined manner across an outer surface of one of the lenses adjacent the field of view corresponding thereto. Each wiper blade unit includes a protective shell portion and a blade portion emerging therefrom to engage the outer surface of one lens. A pair of drive portions are coupled to the chassis, each drive portion engaging one of the slew ring bearings to selectively drive angular displacement of the movable portion thereof. Each drive portion includes a motor actuated drive gear. The lenses are angularly displaced in selectively driven manner relative to the wiper blade units; and, the outer surface of each lens is at least partially wiped by the blade portion of one wiper unit to be cleared prior to advancement angularly into the field of view corresponding thereto.

DETAILED DESCRIPTION OF THE PREFERRED EMBODIMENTS

Briefly, the subject self-cleaning system serves to keep one or more vision protective lenses of a device worn by a user. The system may be implemented on any suitable eyewear or face shield, or other such protective device protectively worn by a user through which a user's field of view must be adequately preserved.

Exemplary applications include, amongst many others, protective goggles or face shields worn by a user while operating a vehicle, participating in an extreme sporting/recreational event, or working in a hazardous environment. The self-cleaning system implemented in protective goggles, for instance, serves to increase visibility while requiring minimal use of the hands by the individual wearing the goggles. The self-cleaning lens goggle integrated system increases visibility by effecting automatic physical wiping of the lenses when selectively (or even adaptively) actuated.

In one illustrative embodiment, this is carried out, preferably, by rotating each of the lenses relative to a wiper member suitably disposed on an outer surface of a lens that is at least partially transparent to clear that portion defining the field of view required for the user. This is preferably at a suitably non-intrusive position, such that the wiper itself keeps from unduly impairing the wearer's field of view.

Figure 1:
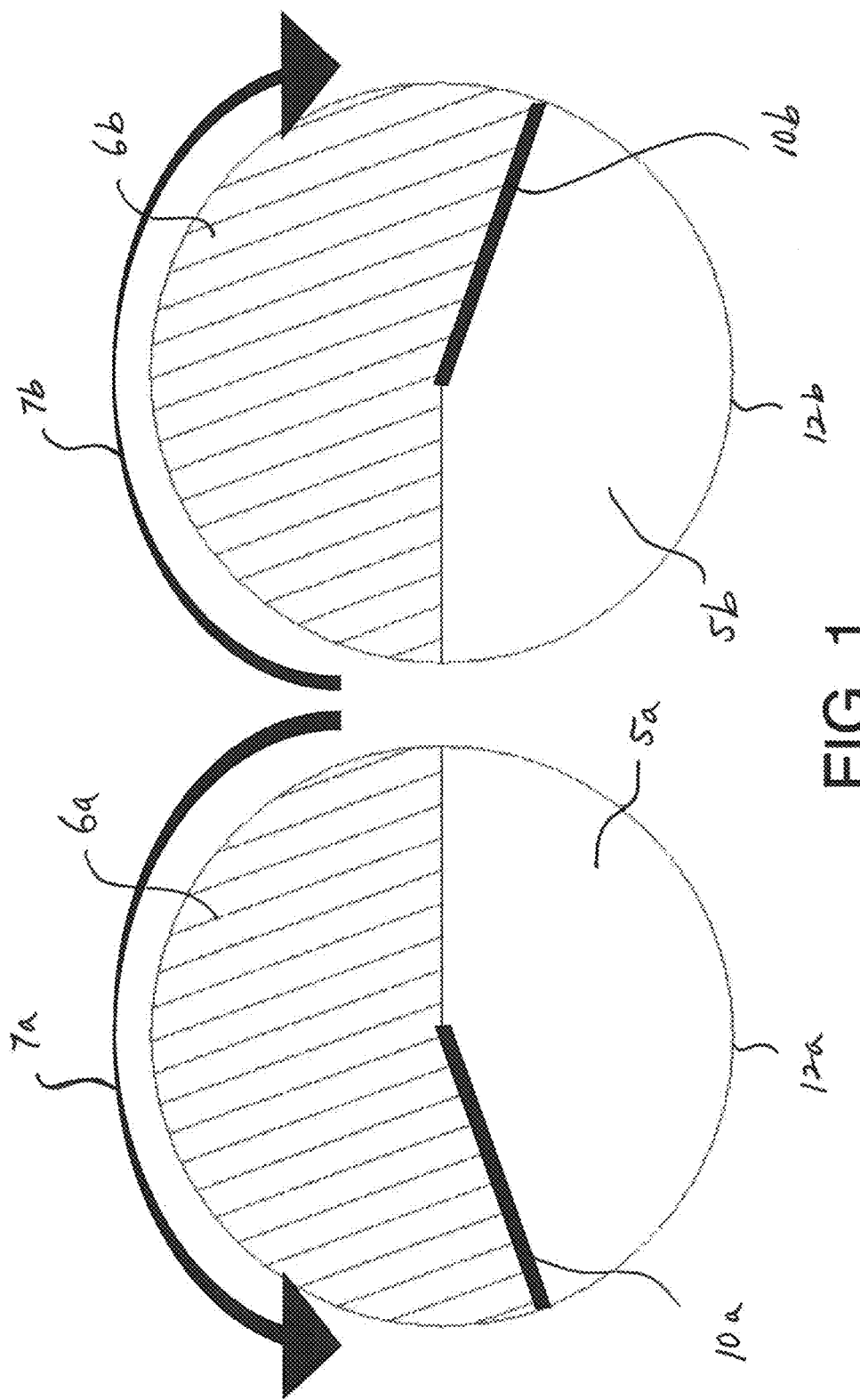
FIG. 1 is a schematic view illustrating certain structural and functional aspects of a system formed in accordance with one exemplary embodiment of the present invention.

Preferably, the lenses in this embodiment rotate while stationary wiper blades remain in contact with and scrape material away from the surface of each lens (as schematically shown in FIG. 1). In alternate embodiments, the wiper blades may be displaced as well. The relative movement between each lens and blade provides cleaning of each lens surface, and the rotating lens surface portions impaired by liquid or debris in the illustrated embodiment are cleared as they pass a wiper blade just before entering the field of view for a given eye. The periodic rotation of the lenses relative to the stationary wiper blades then clears away vision obstructing material (e.g., rain, snow, dirt, mud), as illustrated in FIG. 1. Preferably, the direction of lens rotation and position of the wiper blade are coordinated such that the wiper blades clear the lens surfaces before they advance into the field of view for each eye.

Referring to the exemplary embodiment schematically illustrated in FIG. 1, two wiper blades 10a, 10b are represented by linear strips extending from a central region of each lens 12a, 12b to a point near an outer periphery of the lens. Each blade 10a, 10b in this embodiment runs radially outward, delineating on its lens 12a, 12b a cleared region encompassing the wearer's field of view 5a, 5b (for each eye) from an uncleared region 6a, 6b. In this view, the cross hash marks indicate the dirty or otherwise visually obstructed condition of the regions 6a, 6b, in contrast to the unmarked regions 5a, 5b representing the cleared condition there.

While one wiper blade 10a, 10b is shown employed or each lens in the illustrated embodiment, multiple blades or blade segments may be employed to suit the needs of a particularly intended application. For example, one or more additional wiper blade components may be disposed at regions of the lens surface outside the field of view, so as to provide supplemental pre- or post-clearing of foreign obstructing material from the lens surface.

Also in alternate embodiments and implementations, the blades 10a, 10b may be otherwise configured, positioned, and/or oriented to suit the requirements of the particularly intended application. While shown for example in the illustrated embodiment with both blades extending approximately from the center of each lens radially outward to the lens' circumferential periphery, one or both blades 10a, 10b may be alternatively positioned to extend from a point other than the lens' center to a point variously displaced angularly and linearly therefrom, on each given lens 12a, 12b. Moreover, the wiper blades 10a, 10b need not be symmetrically disposed nor disposed with similar positioning and orientation. Each blade 10a, 10b may be separately and independently positioned/oriented, depending again on the particular requirements of the intended application and needs of the particular wearer.

Likewise, the field of view region 5a, 5b schematically indicated for illustrative purposes in FIG. 1 may be defined with any other configuration suitable for the intended application and/or needs of the particular wearer. The particular shape, size, and position of field of view region on each lens 12a, 12b will depend on such factors as the particular configuration of the given vision protective device, the particular wearer's anatomy, and the particular way in which the given wearer chooses to wear the device.

Preferably, the lenses 12a, 12b are each held by suitable measures to the chassis or other housing of a head-worn device to be rotatable in place. A suitable drive mechanism is employed to actuate automated rotation of the lenses 12a, 12b. Preferably, a drive engagement/linkage between the drive mechanism and lenses is realized through a bearing-type support assembly, but such drive engagement/linkage may in certain embodiments be realized by direct engagement between the drive mechanism and one or more of the lenses 12a, 12b. As the lenses 12a, 12b rotate, any foreign materials collected on an outer surface of the lenses come in contact with the wiper blades 10a, 10b and are thereby caught and diverted away along the lengths of those blades. Dust, dirt, road debris, or the like are forced by the stationary wiper blades 10a, 10b away from areas 6a, 6b of the lens surfaces before those areas advance to be presented at the wearer's field of view 5a, 5b. The lens portions at these regions/areas are effectively cleaned before they are advanced via lens rotation to appear in direct view of the wearer's eyes.

So, converse to a configuration where the wiper blades 10a, 10b wipe liquid or other foreign material away from a lens surface by moving reciprocally back-and-forth, the wiper blades 10a, 10b in the illustrated embodiment preferably remain stationary, while the lenses 12a, 12b themselves are turned along the directions 7a, 7b as needed (relative to the stationary wiper blades) to effect the wiping/cleaning action. Preferably, powered actuation measures are incorporated in the lens housing to turn the lenses.

Turning now to FIGS. 2-5, there is shown a fully assembled system 100 formed in accordance with one exemplary embodiment of the present invention in an illustrative goggles-type application. Generally, an outer casing 102 is formed to house the various mechanical and electrical components of the system, and a headband 104 is secured to the chassis structure 120 to securely hold the goggles on a wearer's head. Automated drive measures in the form of battery-powered drive motors are housed within the outer casing 102 of the system near each rotatable lens 112a, 112b at right and left eye sides of the goggles. The motors automatically drive respective drive shafts which in turn rotate respective drive gears (such as illustrated in FIGS. 6 and 10-12) engaging outer teeth formed on a movable portions of slew ring bearings, which movable portions carry the lenses 112a, 112b. At the outer sides of the frame are formed with two box-like formations, which define internal compartments housing the respective motors for the two lenses. The power source(s) for the motors may also be housed in one or more of these compartments, with the control circuitry also housed in or near one or more of the compartments. A control switch coupled to the control circuitry may be implemented on either side.

A pair of wiper blade units 110a, 110b are fixed to the outer casing 102 at outer ends and extend therefrom transversely across portions of the lenses 112a, 112b. The blade units 110a, 110b are angled preferably as shown, with the outermost end angled, or inclined, downward from the innermost end, so as to help in shedding the residue that collects on the lens surfaces. This results from the angular orientation and location of the wiper blade units 110a, 110b, whose optimal orientation and location may be determined for each particular embodiment and/or application based on observation, experimentation, and applicable know-how.

Suitable measures are employed to guard against potential debris or water/liquid infiltration problem between the lens and the surrounding body of the chassis structure, while preserving sufficient clearance between components for smooth relative movement. For example, the lenses 112a, 112b are kept freely rotatable relative to the supporting components, while the components are packed tightly enough to yield stable fittings and sufficient seal against infiltration of debris or liquid.

Each lens 112a, 112b is preferably served by a wiper blade unit 110a, 110b which extends substantially from the center point of the lens radially outward to a point preferably just beyond circumferential periphery of the lens, and secured to the goggles casing 102 there. Each wiper blade unit 110a, 110b is slanted at an angle (e.g., preferably up to about 45°) sufficient to allow gravity to pull material down and off the lenses during use.

Suitable measures are preferably employed to avoid or at least alleviate the potential buildup of residual debris or other foreign materials against and along the wiper blades. If the lenses 112a, 112b were to have gotten extremely dirty because of rough, splattering travel through a muddy area, for example, the wiper blade units 110a. 110b are suitably configured and oriented (in downwardly angled orientation as illustrated, for instance), such that the accumulated material is readily caught by the squeegee effect of the blades on the lens surfaces, and urged to migrate down along the blades by the collective force of gravity. The pushing agitation of subsequently collected materials with continued turning of the lens surfaces 112a, 112b, and the rush of any oncoming wind (if the wearer is traveling with more than trivial speed) will only aid this process. In typical uses, the collected material does not persist long on the blade units 110a, 110b, as it is swept radially away from the central regions of the lenses by such forces. As described in following paragraphs, moreover, a rear-swept profile of each lens' surface aids in this regard to urge rapid removal of collected material radially outward, guided by the wiper blade units 110a, 110b along their lengths. This is evident in the configuration illustrated in FIG. 2.

What also aids in this regard is a longitudinally extended harness-like protective shell portion in each wiper blade unit 110a, 110b holding a longitudinally extended wiper blade portion which extends transversely downward from the protective shell portion to bear against the lens surface underneath. As shown more clearly in FIGS. 2-4, the blade portion 111a', 111b' (only the right eye side blade portion 111a' being visible in this view, although a corresponding blade portion is held by the protective shell portion 111b) of each wiper blade unit 1110a, 110b is secured to emerge transversely from a protective harness, or shell, portion 111a, 111b, which forms a sturdy sheath covering over the blade portion's length. The protective shell portion 111a, 111b provides stable support, and is preferably configured for simple and convenient replacement of a wiper blade portion (which is preferably formed of rubber or other suitable lens wiping material known in the art). The protective shell portion 111a, 111b is also configured to provide ample overhang laterally beyond the wiper blade portion 111a', 111b' emerging therebeneath to deflect the larger, courser debris away from even contacting the blade itself. With this deflective barrier overhanging the actual blade portion, when heavy amounts of foreign materials are encountered, much of the material built up over the lens surface is essentially pre-cleaned by contact with the leading overhang of the structure. This serves to remove much of the lens surface buildup before it actually hits the blade portions, and the blade portions scrap away only the residual portions nearest the lens surface.

Figure 2:
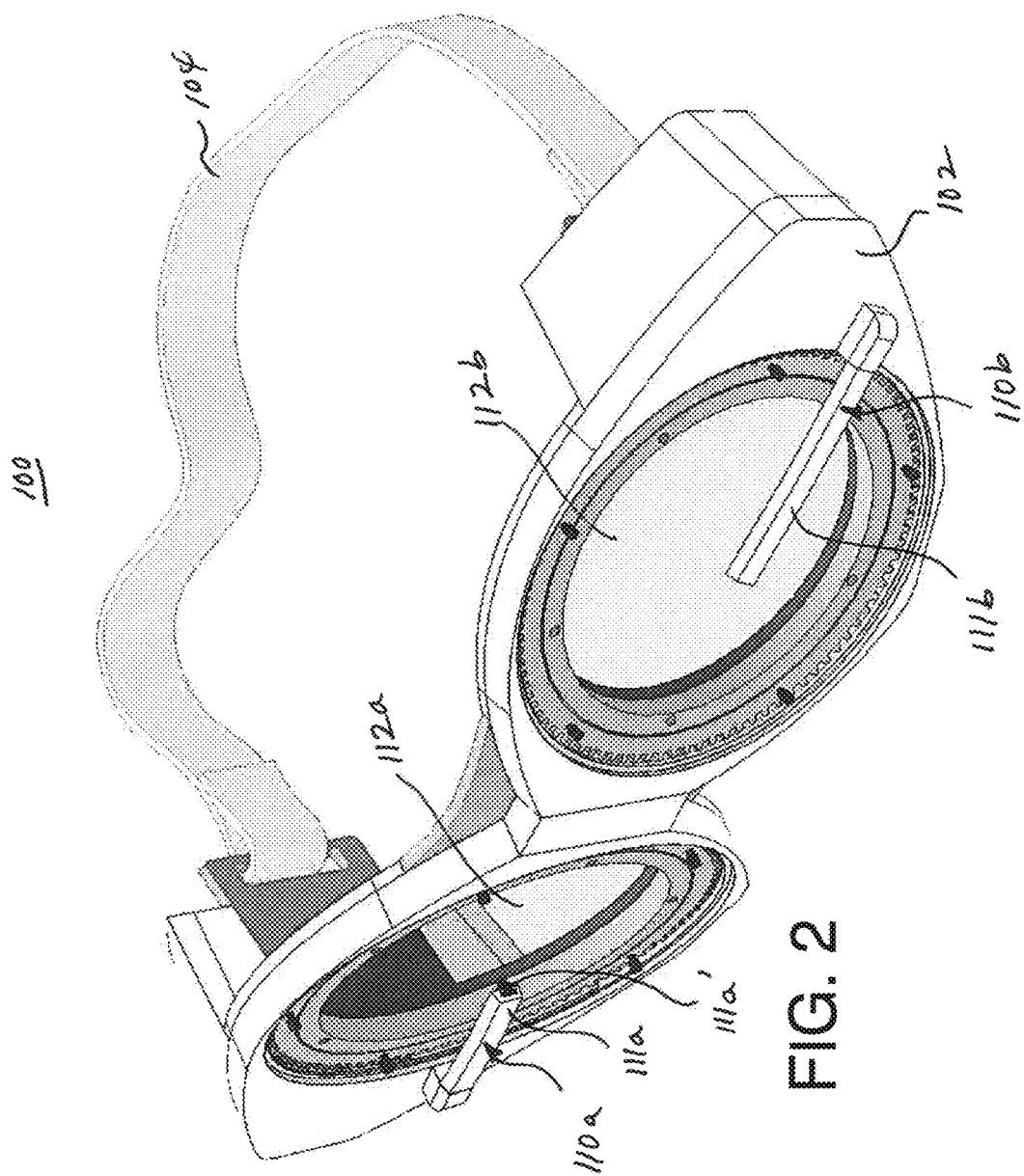
FIG. 2 is a perspective view of a one exemplary embodiment of the present invention as integrated into a goggles type system for self-cleaning a vision protective lens thereof.
Figure 3:
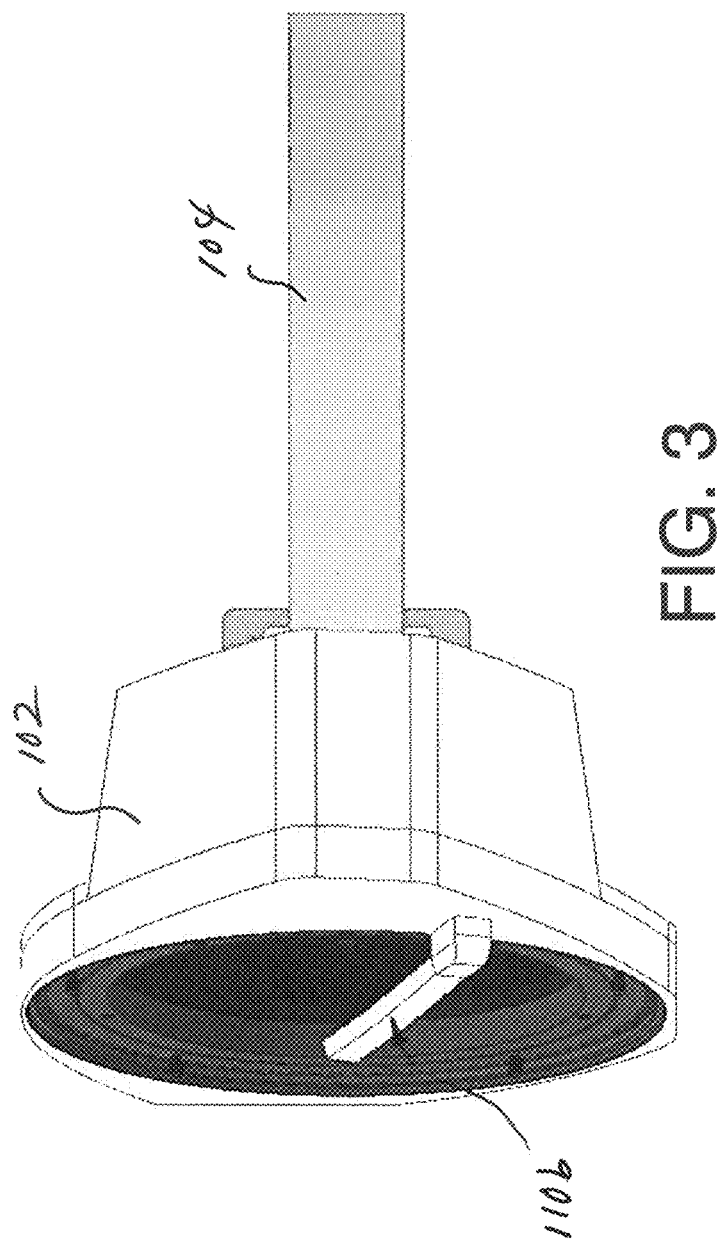
FIG. 3 is a side elevational view of the embodiment illustrated in FIG. 2.
Figure 4:
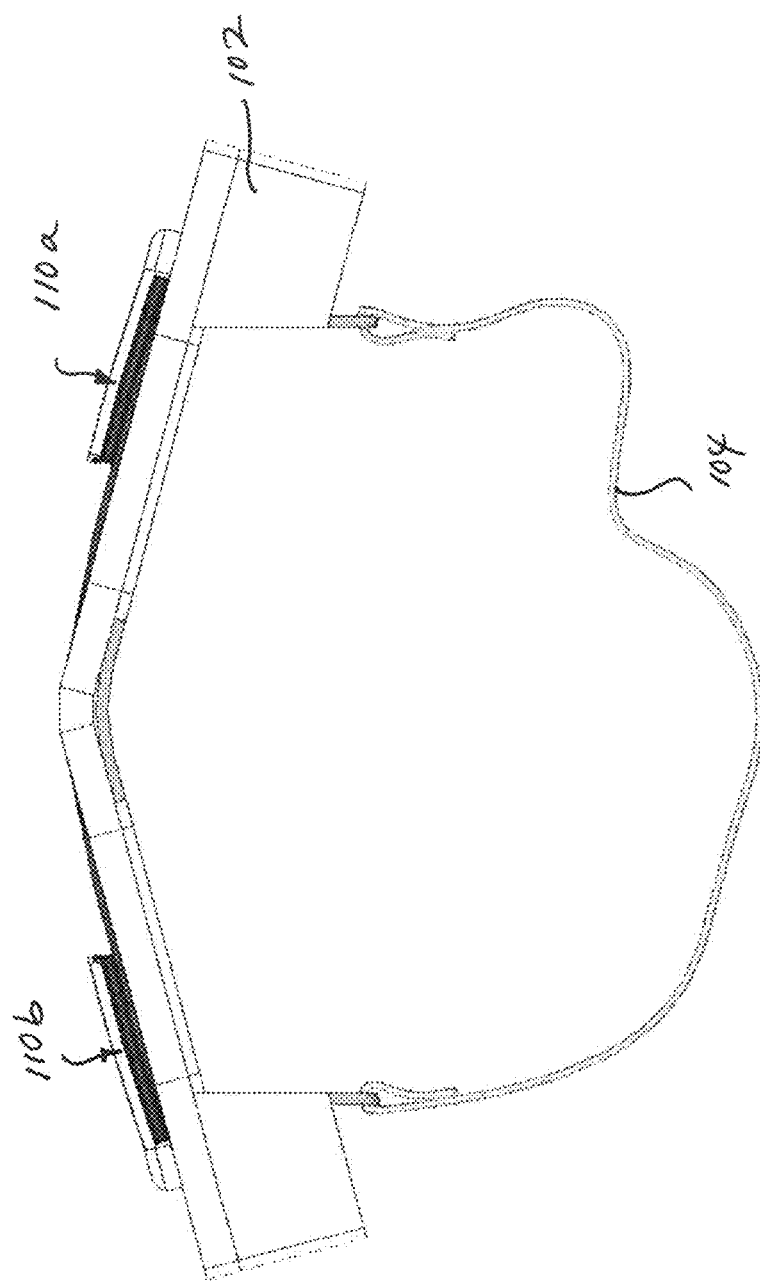
FIG. 4 is a tope plan view of the embodiment illustrated in FIG. 2.
Figure 5:
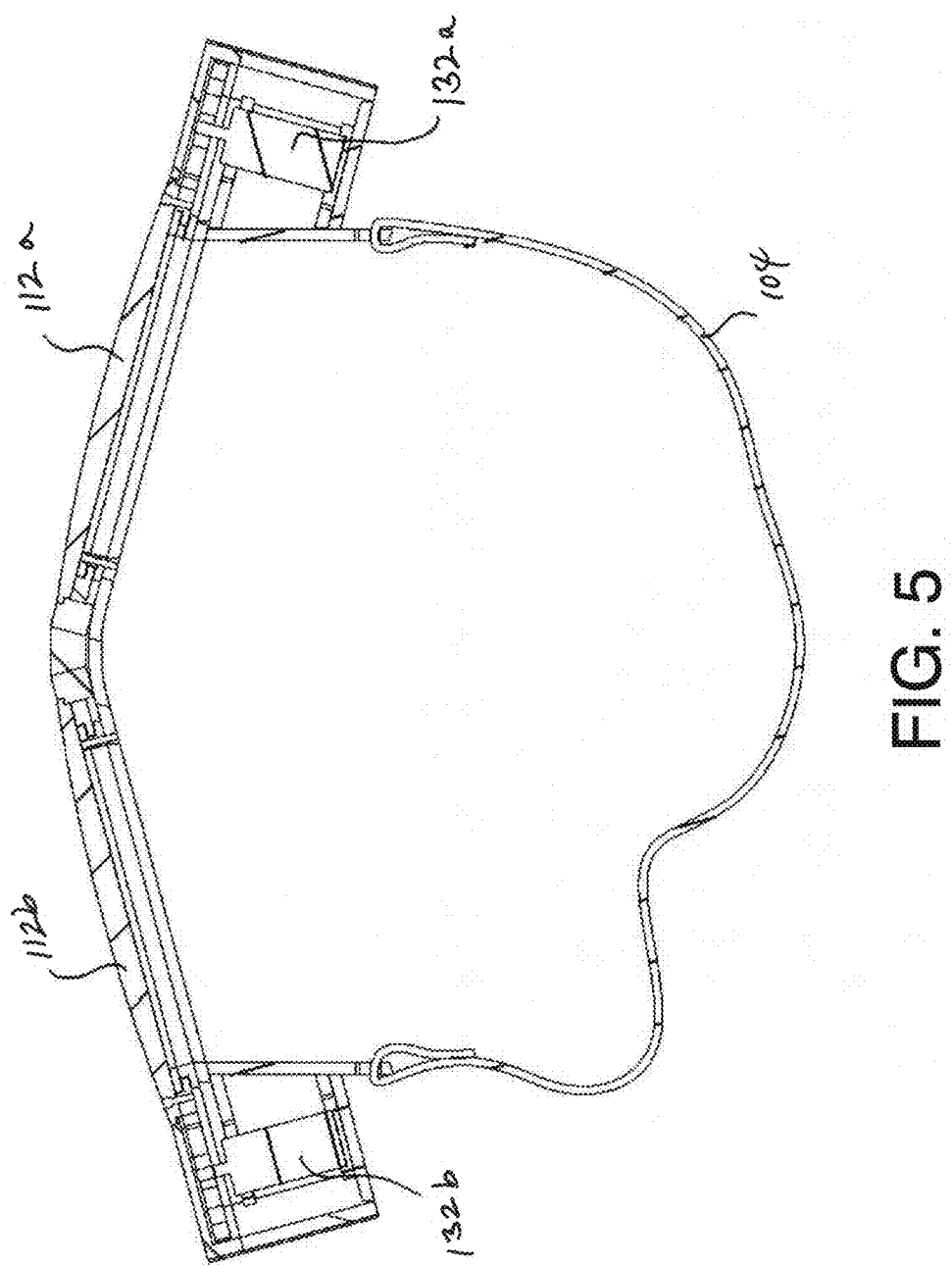
FIG. 5 is top sectional view of the embodiment illustrated in FIG. 2.

As illustrated in FIG. 2, the protective shell portions 111a, 111b are structured to hold and house much of the blade portions 111a', 111b' whose lens-engaging edges emerge from the protective shells' bottom lengths to engage the lens surfaces underneath. Preferably, the tops of the protective shell portions 111a, 111b are configured with suitably sloped profiles to optimize their pre-cleaning, deflecting effect. For example, each of the protective shell portions 111a, 111b is formed in the illustrated embodiment with a beam-like, tubular housing configuration, and is preferably formed with enough body mass surrounding the blade portion itself to ensure that most of the material collected on the lens surface hits the shell structure and guided thereby out of the path of the emergent blade portion that is approaching. The emergent blade portion need only scrape away the residual layer/coating of material, which passes underneath the protective shell portion's overhang (into the housing's clearance over the lens surface).

As noted, each wiper blade unit 110a, 110b is preferably oriented in an angled manner to be slanted radially outward and downward from a central region of each lens 112a, 112b. In the example illustrated, for instance, each wiper blade is oriented at a roughly 30 degree or other predetermined angle downward incline from the lens' central region. With the back-swept lens surfaces (swept laterally outward, for example, from the center nose/bridge area of the goggles), the debris is urged down along the wiper blades by force of gravity as well as radially outward along the back-swept lens surface by force of the oncoming wind or draft.

Alternatively, each lens 112a, 112b may be formed with its center configured to define the most forward tip from which the surrounding surface portions radiating therefrom slope backwards to yield a generally conical, or radially broadened arrow tip-like contour (although preferably without an acutely defined tip or sharply inclined angles). Each wiper blade unit's innermost end is then positioned at or near the front tip and extends radially outward, angling backward on the rear-swept lens surfaces surrounding the tip. This naturally urges any surface liquid or debris back and away from the central/inward regions of each lens surface.

In certain applications, the lenses themselves may be formed with a gradually convex sectional profile. Hence, they are each gradually sloped back a bit from center. This profile would help to serve a similar outward/rearward sweeping purpose.

Preferably, the wiper blades are suitably positioned that they extend across little if any of the wearer's field of view through the lenses 112a, 112b. In certain embodiments, the wiper blade units 110a, 110b may be positioned effectively in an 'eyebrows' configuration—or actually a 'surprised eyebrows' configuration—where the outer tips are directed slightly downward. This defines a ramped structure for liquid or debris scraped from the lens surface to effectively run off and away from the lens' field of view regions. The greater in moisture the material is, the easier it tends to flow over the lens surface then fall off the outermost tips of the wiper blade units 110a, 110b.

Figure 6:
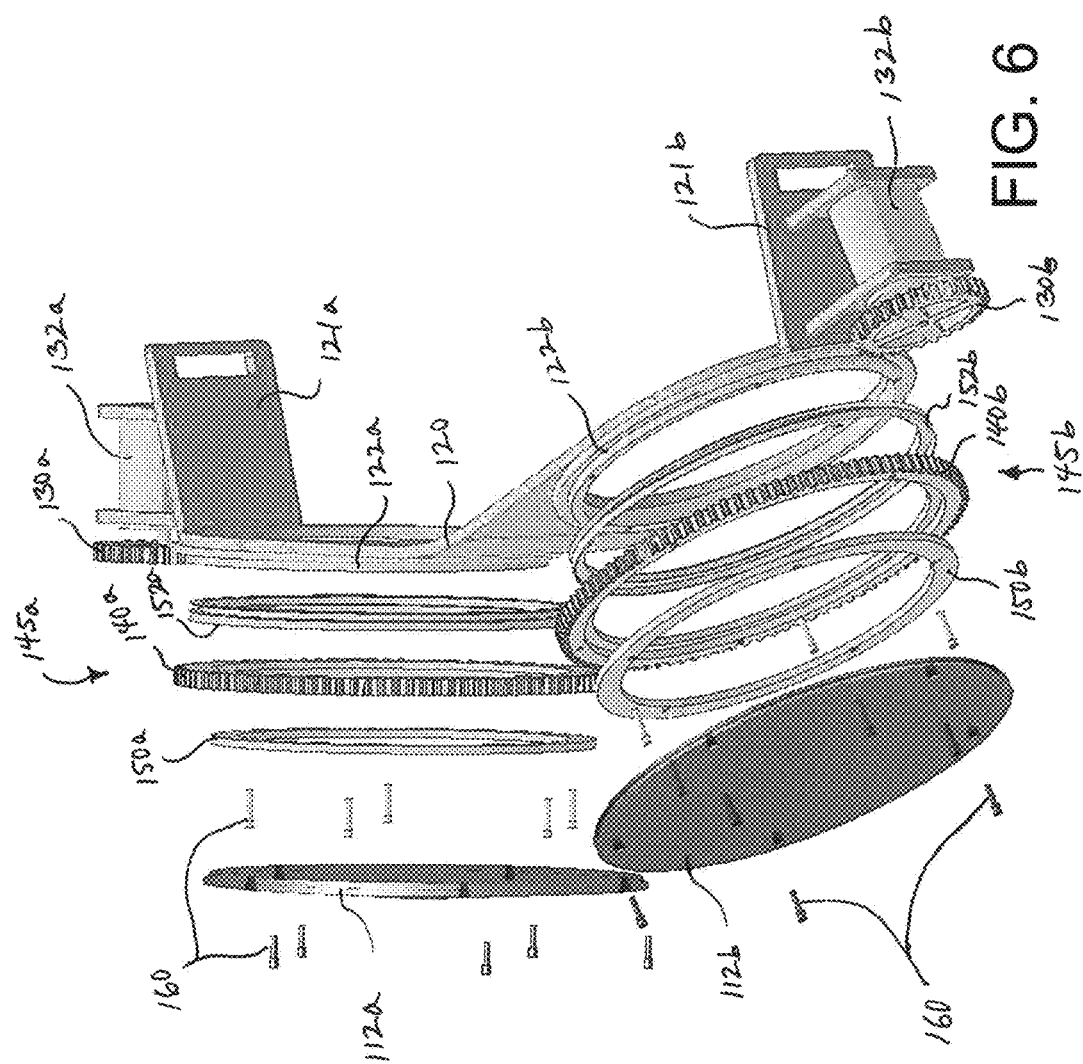
FIG. 6 is an exploded perspective view of a portion of the embodiment illustrated in FIG. 2.

Referring to FIG. 6, there is shown an exploded view of certain components intercoupled to form the wiper-equipped rotatable lens assembly of the goggle integrated system. The rotatable lens assembly serves to carry out the general operation of the illustrated system, wherein the lenses 112a, 112b are actuated to turn relative to the stationary wiper blade units 110a, 110b. In the automatically driven embodiment illustrated, the system includes a chassis structure 120 which essentially holds the various other system components in place, and forms a shield body for the goggles. The system further includes a drive mechanism preferably formed in the illustrated embodiment by a pair of drive gears 130a, 130b each situated at a periphery of a lens opening formed in the chassis structure and driven by a corresponding motor 132a, 132b coupled thereto. Suitable alignment is maintained between the respective drive gears 130a, 130b and a pair of slew ring bearings 145a, 145b for stable and secure engagement of their gear teeth.

Each of the slew ring bearings 145a, 145b is coaxially coupled to an annular seat 122a, 122b formed on the chassis structure 120. The annular seats 122a, 122b extend about respective right and left lens openings formed through the chassis structure 120 and are configured to define stable mounts for the slew ring bearings 145a, 145b. Each slew ring bearing 145a, 145b is formed to include a movable bearing portion coaxially engaged in slidable manner to a stationary bearing portion. The movable bearing portion is thereby angularly displaceable relative to the stationary bearing portion to rotate about a given lens opening of the chassis structure 120. The movable bearing portion carries a lens, and is suitably engaged and driven accordingly by the drive mechanism. In the illustrated embodiment, the movable bearing portion is formed by an externally toothed outer ring member 140a, 140b; and, the stationary bearing portion is formed by the combination of first and second inner ring members 150a/152a, 150b/152b which slidably capture the outer ring member 140a, 140b therebetween.

As described in following paragraphs, each outer ring member 140a, 140b in the illustrated embodiment is intimately coupled to its inner ring members 150a/152a, 150b/152b by a gliding, track-like engagement. The outer ring member 140a, 140b is therefore also referred to herein as an outer track structure, while the corresponding combination of inner ring members 150a/152a, 150b/152b is also referred to herein as an inner track structure.

In the illustrated embodiment, each outer ring member 140a, 140b forming the movable bearing portion is greater in diameter than the inner ring members 150a/152a, 150b/152b forming the stationary bearing portion. But in certain alternate embodiments, the ring member(s) forming the movable bearing portion may be of equal or lesser diameter than the ring member(s) forming the stationary bearing portion, depending on the requirements of the particularly intended application. Hence, the ring member(s) of the stationary bearing portion may in fact form the 'outer ring member(s)' in that case, with the ring member(s) of the movable bearing portion forming the 'inner ring member(s).' The ring member(s) of the stationary bearing portion may thus form the 'outer track structure' in that case, with the ring member(s) of the movable bearing portion forming the 'inner track structure.'

As noted, each outer ring member 140a, 140b in the illustrated embodiment is preferably formed with an external toothed surface circumferentially extending thereabout for meshed engagement with a corresponding one of the drive gears 130a, 130b. Preferably, each slew ring bearing 145a, 145b is sandwiched coaxially between the first inner ring member 150a, 150b and a second inner ring member 152a, 152b, formed in this embodiment with annular contours consistent with the outer ring member 140a, 140b. The first and second inner ring members 150a/152a, 150b/152b at each of the right and left eye sides are secured by suitable fasteners 160 (such as screws) to a corresponding annular seat 122a, 122b of the chassis structure (or shield body) 120. The outer ring member 140a, 140b at that side is slidably captured therebetween for smooth angular displacement about the lens opening defined by the annular seat 122a, 122b. The lenses 112a, 112b are each secured by suitable fastening measures 160 to a corresponding one of the outer ring members 140a, 140b to rotate with that outer ring member 140a, 140b when angularly driven by actuation of the motor/drive gear combination.

Each outer ring member in the illustrated embodiment is slidably captured between and about portions of the first and second inner ring members for rotational displacement relative to both. But in certain alternate embodiments, one of the inner ring members may form a part of the stationary bearing portion, and the other inner ring member may form a part of the movable bearing portion. That other inner ring member may then be configured to serve as an annular retention cover that slidably engages the stationary inner ring member. The outer ring member 140a, 140b may then be secured to this annular retention cover for angular displacement therewith relative to the stationary inner ring member. Each lens 112a, 112b may then be fastened by screws or other suitable measures 160 onto either the outer ring member 140a, 140b or onto the annular retention cover. The annular retention cover would then serve much as a turn table for the lens 112a, 112b and outer ring member 140a, 140b carried thereon.

Depending on the tightness of the seal as implemented, the resulting structure may or may not prevent all air from passing through the intercoupled components. Regardless, the resulting structure would effectively keep debris, dirt, and material of that nature from infiltrating the area protected by the goggle's shield body and lenses.

The various system components may be formed of any materials or combinations of materials known in the art to suit the requirements of the particularly intended application. The chassis 120 and slew ring bearing 145a, 145b components are preferably formed of plastic or other such materials having high strength to weight ratios and ease of workability. The first and second inner ring members 150a/152a, 150b/152b are preferably formed of, or have at least their engaging contact surface portions lined with a friction-minimized plastic bearing material of any suitable type known in the art to permit sufficient gliding contact that obviates the use of extraneous lubricating agents. One example is a plastic-based bearing material available under the commercial name IGUS or IGLIDUR. The lenses 112a, 112b may also be formed of a plastic-type or any other suitable type of material known in the art. Other than the headband and electric motors, and perhaps the fasteners in certain embodiments, the various components of the goggle integrated system may be similarly formed of suitable plastic-type materials.

Figure 7:
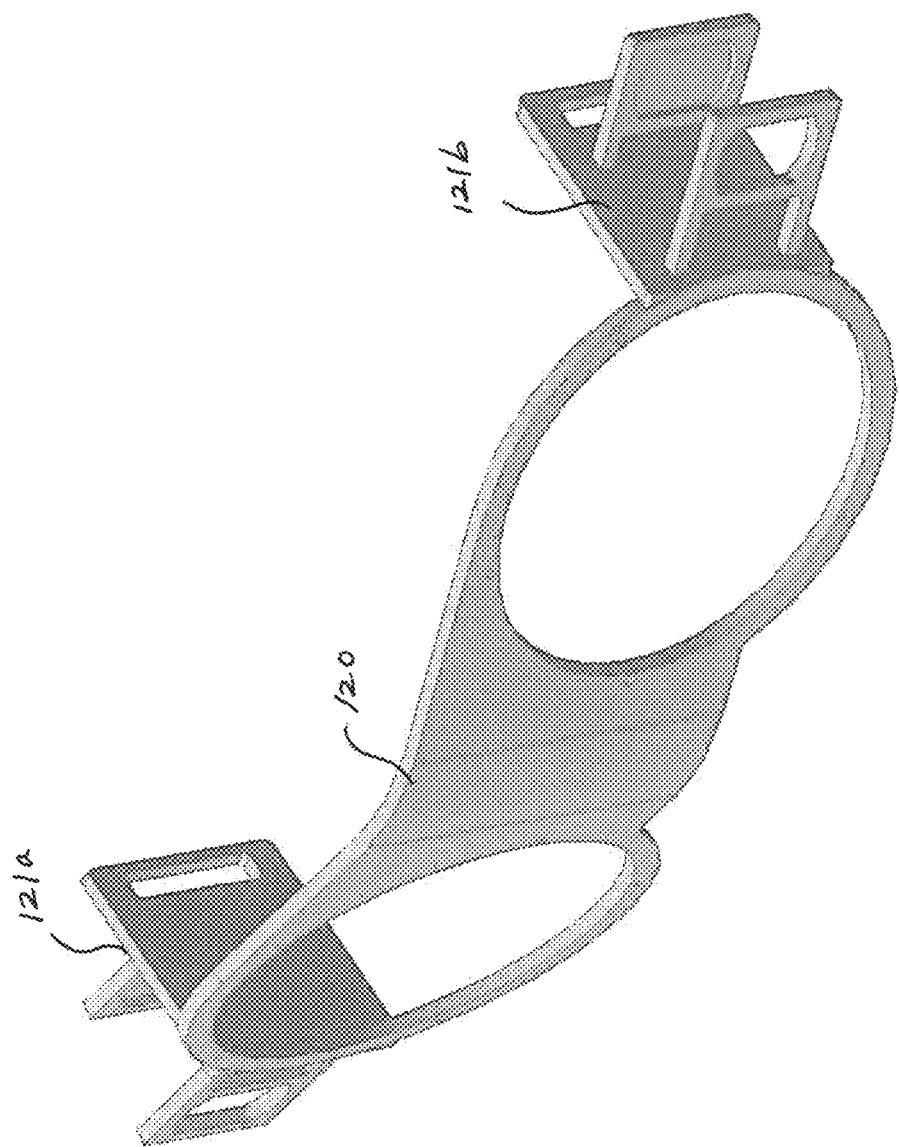
FIG. 7 is an isolated perspective view of a portion of the embodiment illustrated in FIG. 2.

Turning now to FIG. 7, the chassis structure 120 is shown in isolation. This structure 120 provides direct or indirect support for all system components in the disclosed embodiment. The supported components include the wiper blade units 110a, 110b, which are supported in the illustrated embodiment by the chassis structure 120 on or through the outer casing 102. The chassis structure 120 is preferably though not necessarily formed integrally, with a pair of side wing portions 121a, 121b extending from the main shield body portion. The integrally formed structure serves in many applications to optimize strength and integrity of support provided by the chassis structure 120. The side wing portions 121a, 121b provide stable and secure mounting support for the motors 132a, 132b and respective drive gears 130a, 130b. The shape, size, and other configurational features of the chassis structure 120 determine the shape and position of the system's field of view 5a, 5b through the lenses 112a, 112b when the system is fully assembled.

The chassis structure 120 is shown in FIG. 7 without the annular seats 122a, 122b. For simplicity of structure and ease of manufacture, the annular seats 122a, 122b which provide for conveniently aligned mounting engagement of the slew ring bearing and bearing member assemblies to the chassis structure 120 are preferably formed separately and fastened to that chassis structure 120.

Figure 8:
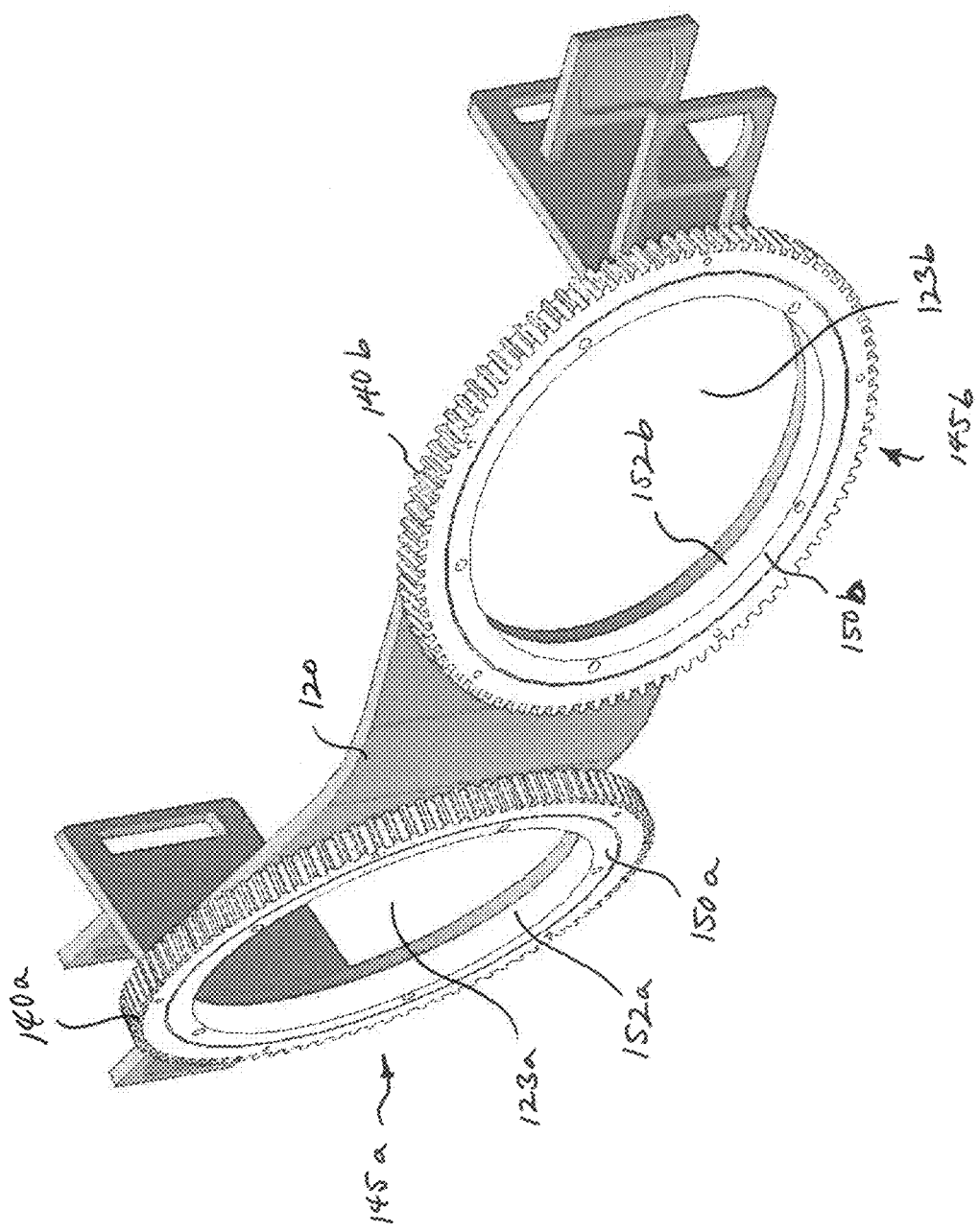
FIG. 8 is an isolated perspective view of certain combined portions of the embodiment illustrated in FIG. 2.

FIG. 8 illustrates the chassis structure 120 equipped with the annular seats 122a, 122b (not visible in this view) to which the slew ring bearings 145a, 145b are coupled. The outer ring members 140a, 140b are shown rotatably assembled to their corresponding inner ring member combinations 150a/152a, 150b/152b. As noted, when such outer and inner ring members are packed together and coupled to the chassis structure 120 (at each of its annular seats 122a, 122b), the resulting assembly about each lens opening 123a, 123b may be considered as the coupling of an outer track structure annularly engaging a coaxial inner track structure. An outer track structure is thus effectively formed by the each outer ring member 140a, 140b, which encircles and slidably engages a coaxial inner track formed collectively by the first and second inner ring members 150a/152a, 150b/152b. The inner track structure is in turn securely coupled to the chassis structures annular seat 122a, 122b.

Figure 9A:
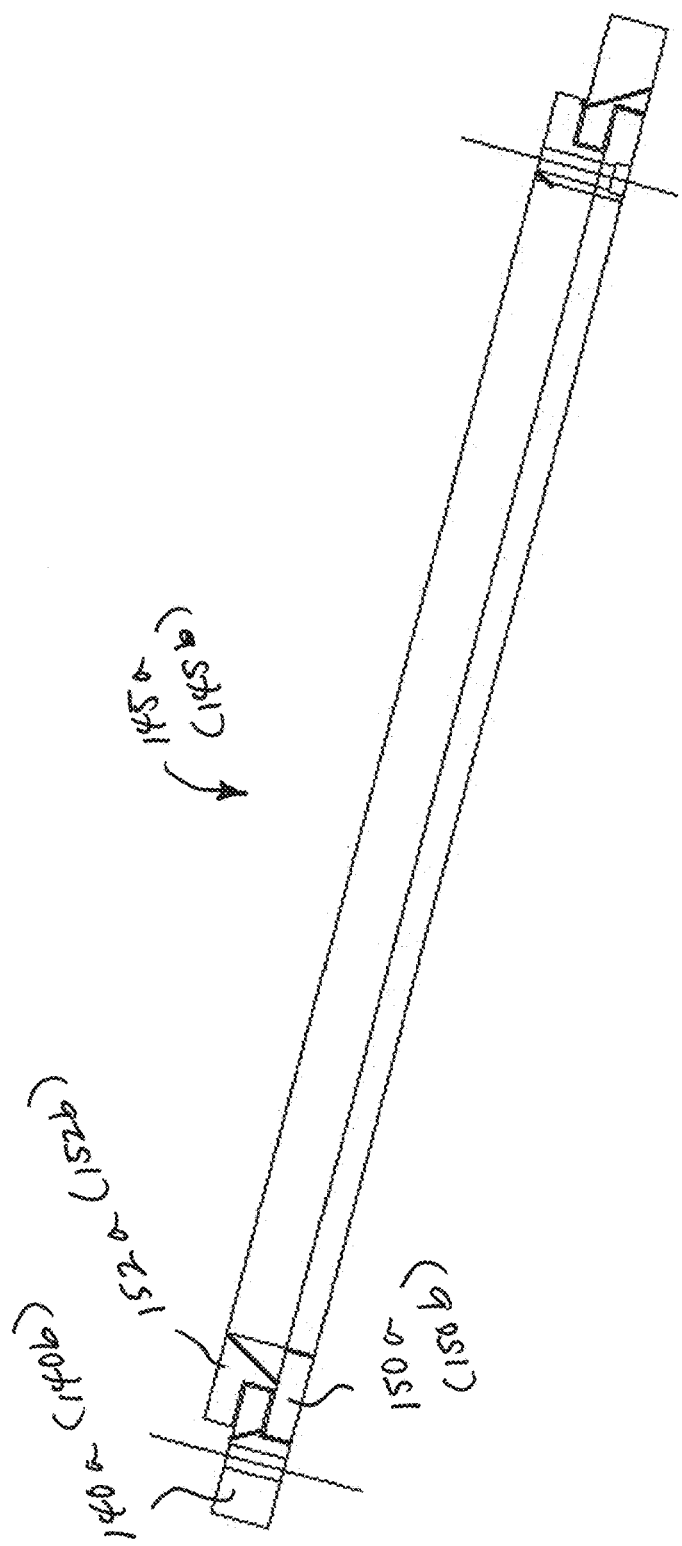
FIG. 9A is a sectional view of a portion of the embodiment illustrated in FIG. 2.
Figure 9B:
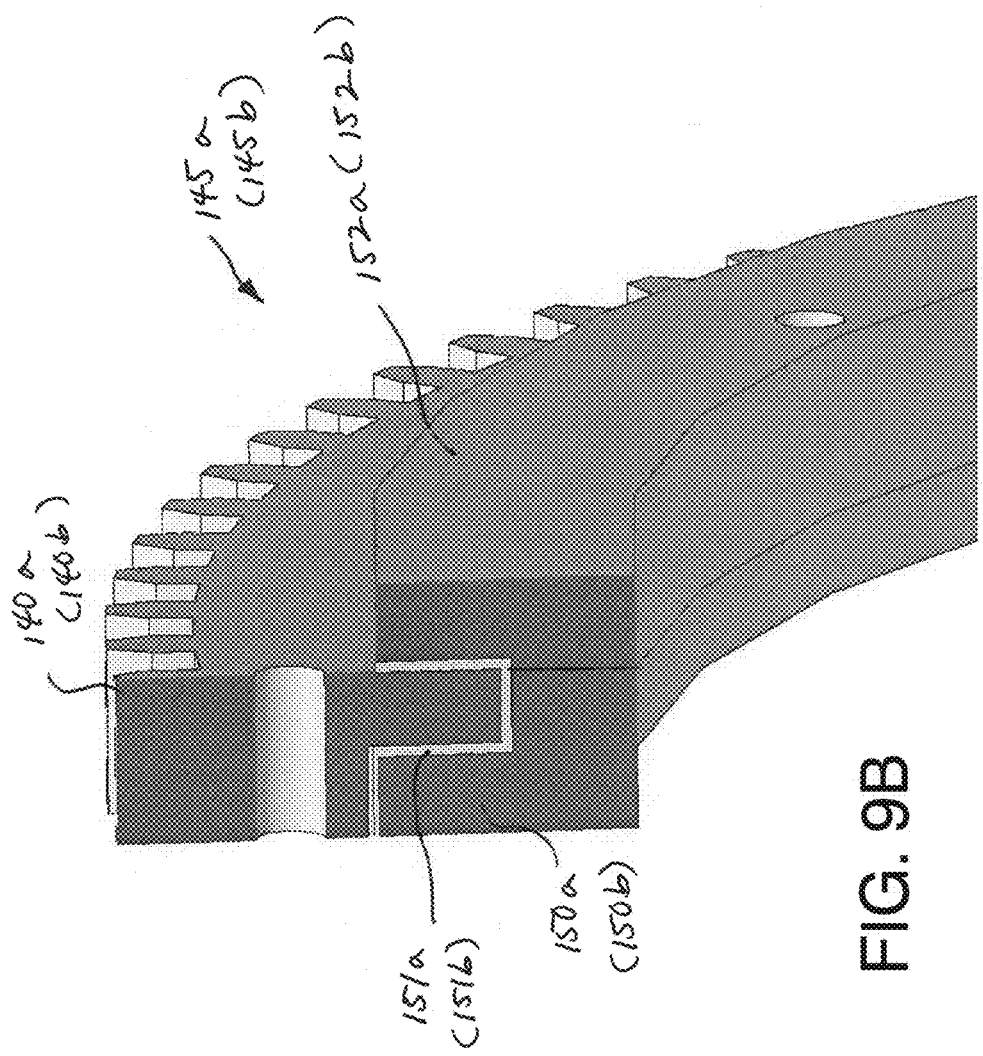
FIG. 9B is a detailed sectional view, partially cut away, of the portion of the embodiment of FIG. 2 shown in FIG. 9A.

As illustrated in the sectional views of FIGS. 9A-9B, the outer track structure engages the inner track structure at a gliding interface 151a, 151b. This gliding interface is preferably a friction-mitigated interface (between the outer track and inner track structures' slidably engaging surfaces) realized without an extraneous lubricating agent. Whether dry or wet, an extraneous lubricating agent poses the risk of leakage and escape which could obstruct vision and pose a hazard to the wearer's exposed eyes, unless additional, often elaborate measures are taken to guard against such leakage and escape. As described in preceding paragraphs, the gliding interface 151a, 151b may be realized by separately inserting, or lining (or otherwise forming) at least one of the engaging components at the interface with, an element formed of any suitable solid friction reducing material known in the art. For example, the element may be formed of a solid plastic-like material known in the art which enhances surface gliding effect, minimizing friction with properties to abate the buildup of heat while avoiding the mess of wet lubricants or dry powdery lubricants. One such material is a plastic based slide bearing/glider material commercially available under the name IGUS or IGLIDUR, among others. This approach is preferable over other friction reducing mechanical measures such as roller bearings or the like.

This sliding element, or slide bearing, at the gliding interface 151a, 151b is of such properties that it tolerates considerable rubbing, while maintaining smooth, low friction surface contact. As such, it mitigates heat buildup which tends to increase proportionally with friction (that is, the less the friction, the less the heat buildup). The sliding element overlays, to effectively coat, the interfacing/opposing surfaces of the inner and outer ring members to serve much as a lubricant-like buffer between surfaces that would otherwise rub together destructively over repeated use.

Preferably, suitable measures are taken to ensure sufficient seal at coupling points and joints between goggle integrated system components. In particular, structural measures are taken to ensure sufficient seal to prevent undue air passage or seepage of liquid or debris between the lens and the goggle housing or slew ring bearings, or between a slew ring bearing's inner and outer ring members. The inner and outer ring members of the slew ring bearing are coupled in such manner as to preserve both intimate slidable coupling and tight seal.

Referring again to the sectional views of FIGS. 9A-9B in this regard, the inner and outer track structures formed by the inner ring and outer ring members capture the gliding interface 151a, 151b which effectively forms a sliding element therebetween. This sliding element is configured to define a sectional contour having multiple bends extending from an inside surface of the lenses towards an interior side of the goggles. As such, the sliding element not only provides a solid lubricating liner between the inner and outer tracks of each slew rate bearing, but also serves as an insert that follows an intrusion-resistant, serpentine sectional profile to substantially fill the gap extending between the tracks and ensure sufficient seal.

In the sectional views of FIG. 9A-9B, a lens section is preferably attached to extend over and cover the joint between relatively movable inner and outer track structures of the slide bearing assembly. For liquid to seep through the joint between the combined assembly components, it would have to work its way around and under the lens section surface, then through the intermediate space filled by these slide bearings, which space follows a meandering contour (sectionally) from back side of the lens section.

As illustrated in the various views, each lens 112a, 112b is attached to an outer track structure of a slew ring bearing 145a, 145b. Each lens at the points of attachment to the outer track structure preferably is of similar diameter if not equal diameter as that outer track structure. Drawing axially away from the outer ring, however, the lens flares out peripherally so as to preferably define a curved sectional contour, with peripherally overhanging extremities, or flange-like portions, which partially overlap the surrounding casing/housing parts of the goggle integrated system. The overlap means if there is moisture that is going to infiltrate the goggles, the moisture must flow around the outer peripheral flanges, work its way underneath, then migrate along the lens walls and somehow make its way also through the intermediate area sealed by the slide bearing assembly.

As noted, this seal is formed in each slide ring bearing, and its tight friction-reduced coupling, where little if any empty space is left between movably interfaced components. The resulting structure forms virtually an O-ring, having combined sealing and lubricating effect not defeated or diminished by water, dirt, or debris.

Multiple points of the disclosed goggle integrated system are preferably formed with outer components, like the lens, which are configured to incidentally serve much like a flashing, or as some sort of flange structure. This makes it difficult for moisture to get from the outside of the goggle integrated system to the inside (protected) area about the wearer's eyes. The moisture would have to get past a number of such flashing type structures and work through very intimately sealed spaces. That is not likely to occur in most normal applications.

As shown, a separate slide ring bearing 145a, 145b is provided for each independently rotatable lens 112a, 112b in the illustrated embodiment. The inner track slidably supporting the outer track in each slide ring bearing 145a, 145b is formed by the concentrically coupled first and second inner ring members 150a/152a, 150b/152b, one of which is affixed to the chassis structure. Each of the outer ring members 140a, 140b preferably carries one of the goggle lenses 112a, 112b in this particular embodiment. But in certain alternate embodiment, the lenses 112a, 112b may be carried alternatively on one of the first or second inner ring members which is then affixed for movement with the outer ring member 140a, 140b. Either the outer ring member or the movable inner ring member affixed thereto is then formed with a toothed surface accordingly configured to be gear-driven by the motorized drive measure (drive gear 130a, 130b and motor 132a, 132b). Responsive rotation of the toothed bearing/member would then turn the lens carried thereon.

Figure 10:
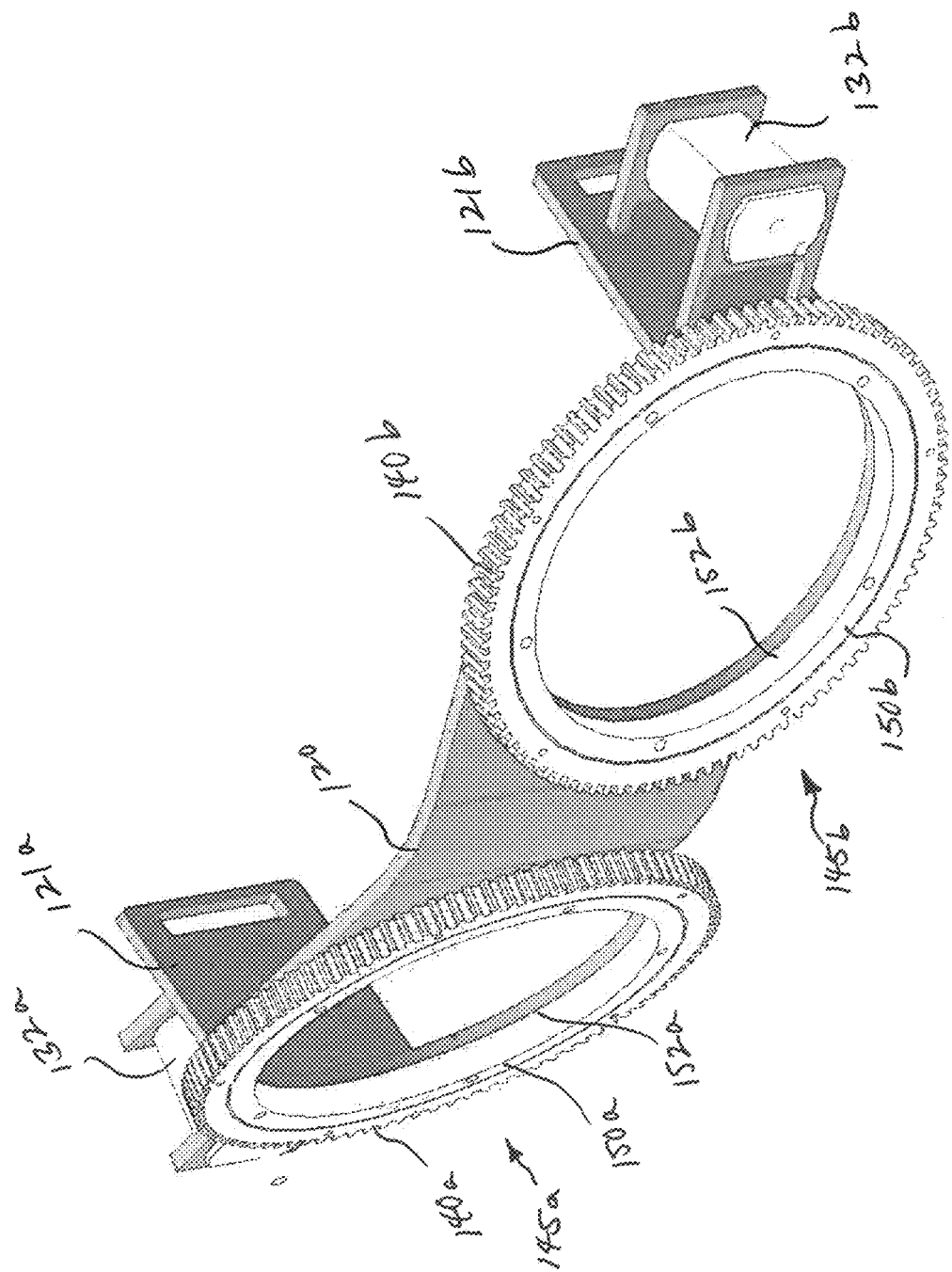
FIG. 10 is an isolated perspective view of certain other combined portions of the embodiment illustrated in FIG. 2.
Figure 11:
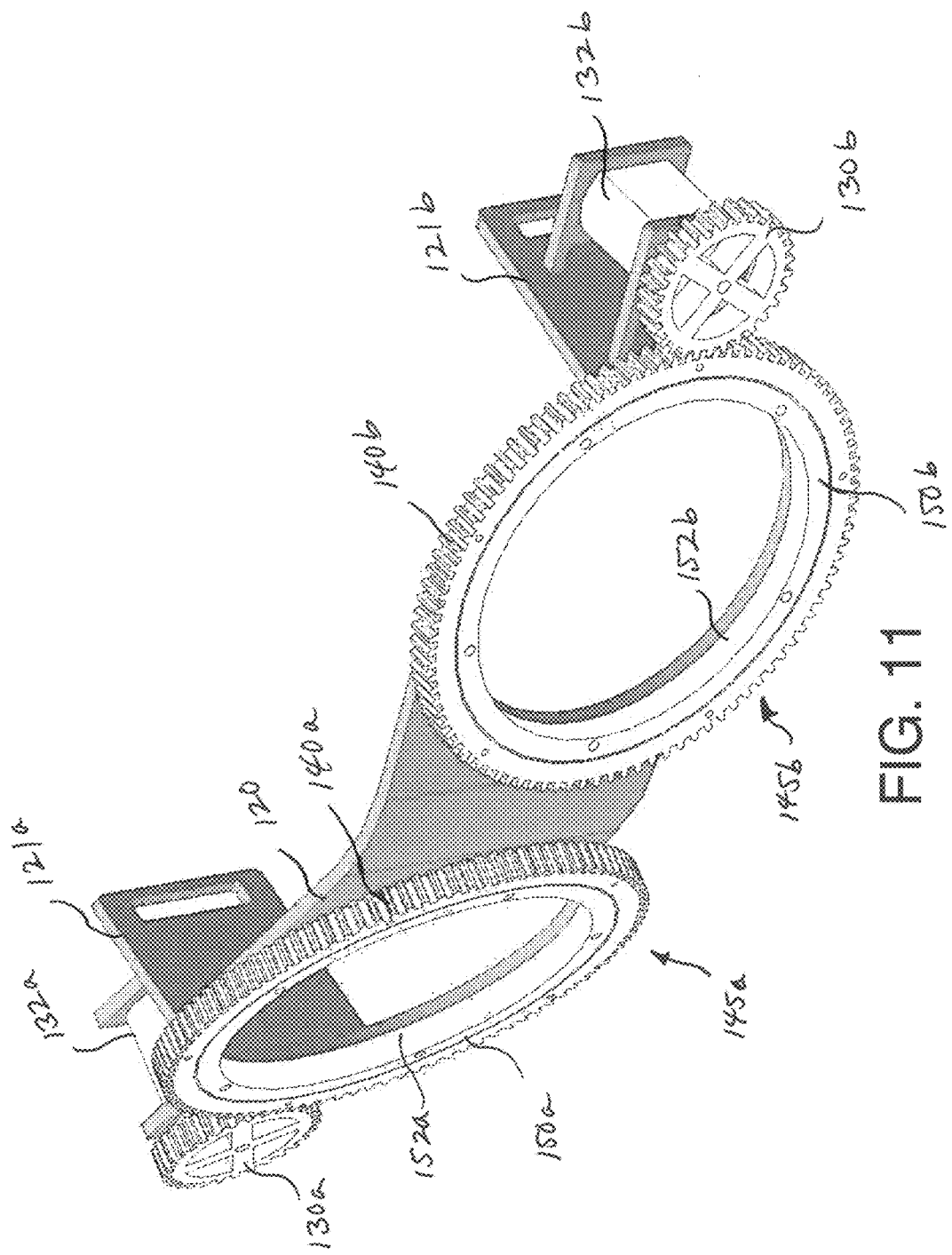
FIG. 11 is an isolated perspective view of certain additional combined portions of the embodiment illustrated in FIG. 2.
Figure 12:
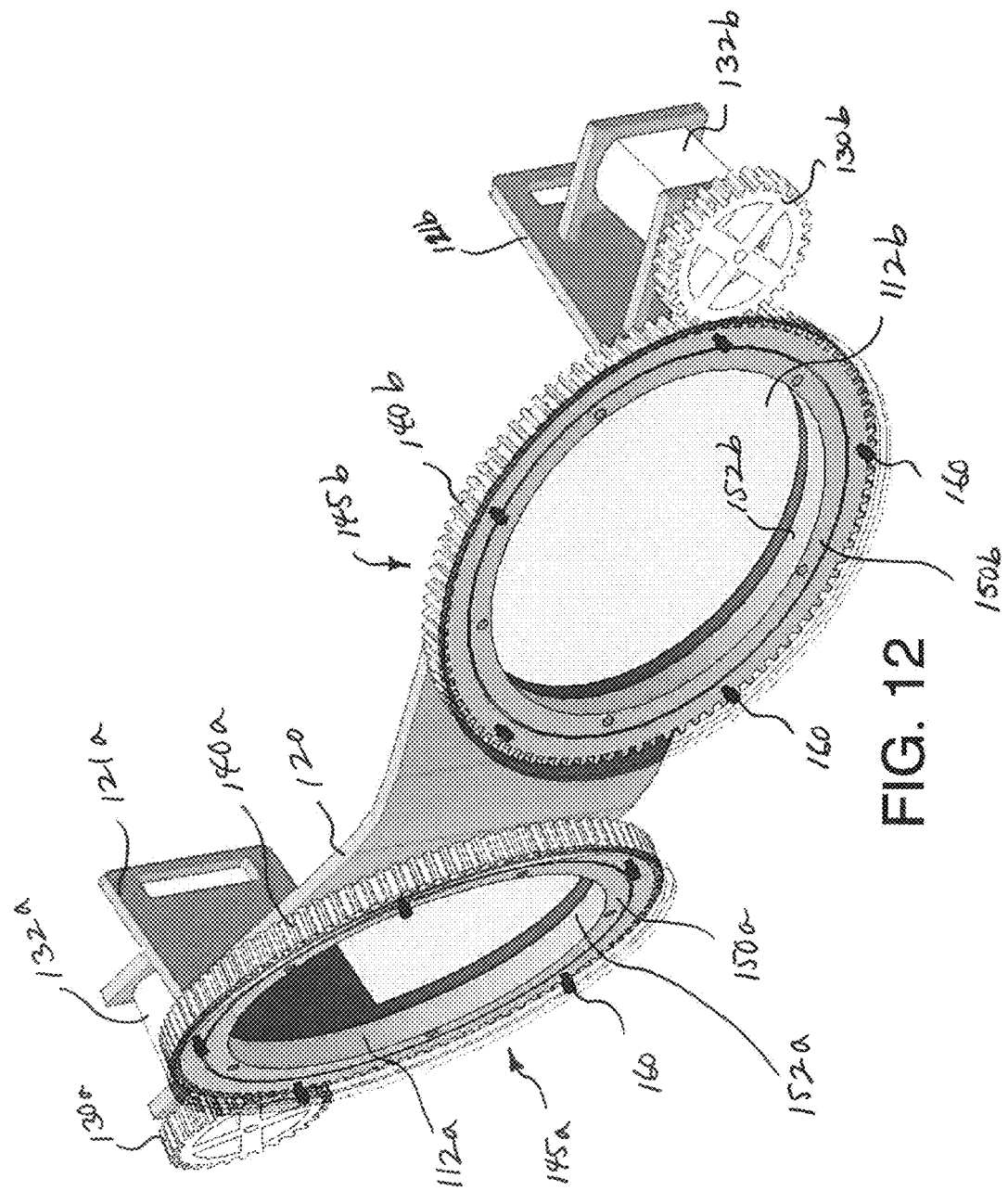
FIG. 12 is an isolated perspective view of certain further combined portions of the embodiment illustrated in FIG. 2; and, FIG. 13 is a schematic view illustrating an electrical intercoupling of certain portions of a system formed in accordance with a certain exemplary embodiment of the present invention.

Referring more specifically to each outer ring member 140a, 140b in FIGS. 10-12, the toothed surface on the outer track formed thereby is engaged and driven by suitable drive gearing member(s) connected to one or more electric motors. One or more electric motor drive measures or any other suitable drive measures known in the art are disposed on the chassis structure 120 to drive suitable gearing elements which engage the outer gear teeth of the outer ring member. The inner track is fastened or attached to the chassis structure and is thereby held stationary on that chassis structure, while the outer track (the outer ring member in this embodiment) is free to rotate thereabout. Thus, the inner track serves to provide a retentive annular support on which the outer track turns. The annular engagement between the concentric inner and outer tracks is preferably both sealed and tight, such that the rotation yields smooth turning of the lens, without undue wobbling.

In certain embodiments such as illustrated in FIGS. 6 and 10-12, a separate independently actuated motor 132a, 132b is provided individually for each rotatable lens 112a, 112b. The chassis structure 120 is built with suitably configured outer supports extending from the side wing portions 121a, 121b where the individual motors 132a, 132b for each right and left side are held. The motors 132a, 132b, chassis structure 120, and casing 102 are each configured and dimensioned to accommodate the wearer's anatomical characteristics, so that the goggle integrated system comfortably fits the wearer's head and face in comfortable yet conformed manner.

Other optional components of the goggle integrated system not specifically shown or described in detail herein include:

1. An inner cover which conforms to the shape of a wearer's face (e.g. forehead, cheeks, and nose) to enhance comfort and optimize fit.
2. Foam padding disposed as needed on the chassis structure and/or outer casing to provide close intimate fit to a wearer's face without compromising comfort.
3. Localized enclosure panels configured to cover and protect the drive gears and electric motors from external or infiltrating elements.

Figure 13:
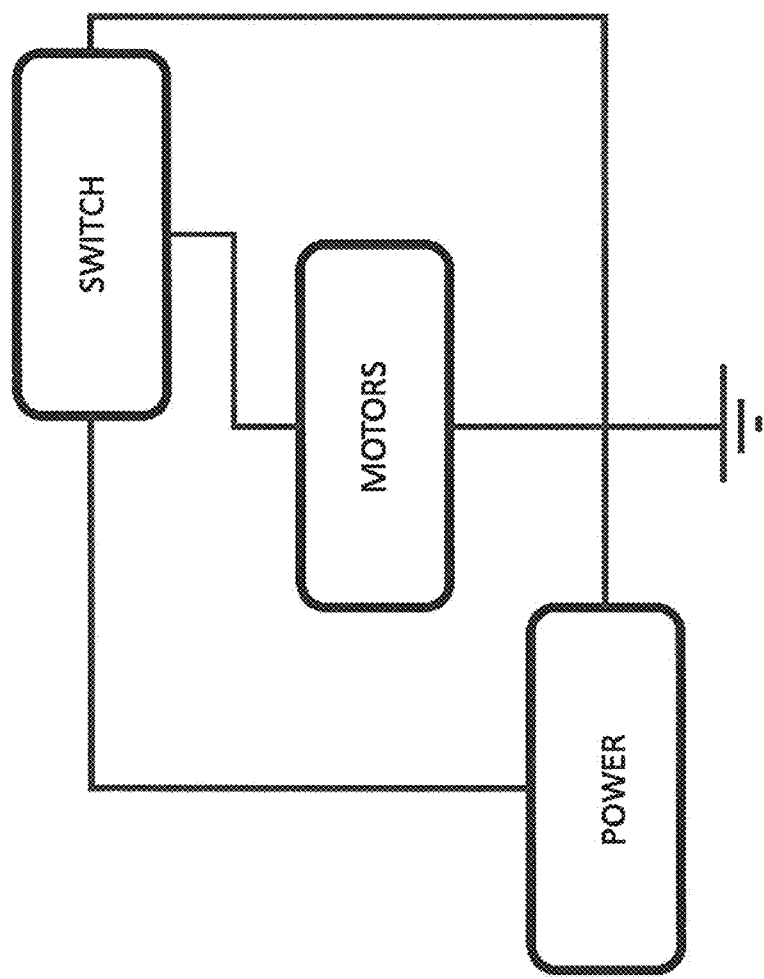

Referring now to FIG. 13, a high level schematic block diagram of functional components/modules is illustratively shown for one exemplary embodiment of the goggle integrated system. As illustrated, an electromechanical switch of any suitable type known in the art, with optional protective fuse, is employed. The switch may be of manually actuated type with a flip switch mechanism suitably disposed on the goggle's outer casing. The switch may also be of the remotely operated type, with a manual actuator member located on the goggle wearer's belt or other equipment or accessory within his/her convenient reach.

The power source may include just one power unit shared by both lenses' rotation mechanisms, or may include separate power units for the two sides. For example, the power source may be formed by one battery or multiple batteries whose supply lines split out to each side of the goggle integrated system to dual motors—an electric motor on each side. For simplicity, they are represented in the block diagram grouped together. The power is distributed accordingly to the motors through the control switch, with the optional fuse protecting against electrical overload conditions.

The electric motors employed are preferably compact, quiet, and produce minimal vibrations, and deliver sufficient torque and moderate rotations per minute (RPM) without generating excessive heat or consuming excessive power. Preferably, the drive gears are formed with minimal diameter relative to a slew ring bearing, and their gear teeth align and mesh efficiently with the gear teeth formed on the slew ring bearing.

A portable battery is preferably employed, and a control switch preferably enables selective actuation of different modes of operation. The selectable modes, for example, include:

1. Off mode where power to the drive gears is cut off
2. Continuous Mode where substantially constant moderate power is supplied to energize the drive gears.
3. Burst Mode where supplied power alternates between off (e.g. 30 seconds) and maximum (e.g. 5 seconds).

One or more motors either shared by or individually dedicated to the multiple lenses is/are controlled by a switch, as shown in the simplified schematic diagram illustrated FIG. 13. The system is not limited to any particular type of motor or other such drive mechanism. Whatever mechanism is sufficiently lightweight, quiet, low in vibration, or otherwise fit for the intended application would be suitable. Preferably, an optimal combination of battery duration, power level output, and other parameters would be selectively set based on weight and other factors of importance to the intended application.

Various modifications from the illustrated embodiment may be incorporated in alternate embodiments. For example, instead of the drive gear and shaft configuration for each rotatable lens as shown, the drive shaft may be formed by a worm gear which directly engages the teeth (or other suitably configured threads) formed on the slide bearing assembly's (formed for example by the slew ring bearing and annular bearing members) movable track structure. Furthermore, while the movable track structure of the slide bearing assembly is shown to be the outer track structure in the disclosed embodiment, the movable member may alternatively be the inner track structure, with the outer track structure remaining stationary. Another variation may be the use of common drive gearing disposed for instance between the two rotatable lens portions instead of using independent drives for each rotatable lens portion. Also, in place of drive gearing to transmit the drive power to the movable track structure carrying a lens, a drive belt linkage or the like may be employed instead.

In addition, the shapes of the lenses are not limited to just the generally circular shape shown. As long as the rotation of one lens doesn't interfere with the other, or is not obstructed by the other components, various other shapes may be employed to suit the particularly intended application.

Actuation control is preferably provided by a switch operably coupled to the motor(s) employed in the self-cleaning system. While not shown, any suitable switching mechanism known in the art may be employed. The switching mechanism may reside on the chassis, directly provided on the motor(s), or maybe intercoupled through hardwired or even wirelessly linked control measures.

The motor(s) or other drive mechanism employed is preferably energized by portable battery power. Such battery power source may be disposed within the goggle casing about the chassis, near the electric motor(s). The battery power source may also be attached at other points, such as on the head band.

Conceivably, the bulkiness and weight of the goggle casing or the shell may be of practical concern. Acceptable placement and accommodation of the battery power source may be determined based on the requirements of the particularly intended application. In certain cases, where the application permits, drive power may be obtained by interconnection to a vehicle power source, obviating the need to carry a portable power source on the self-cleaning system itself.

Applications of the disclosed self-cleaning system include various activities, including occupational, vocational, sporting, and recreation. Among them are goggle integrated systems worn by participants of such activities as snowmobiling, skiing, motor cross, military exercises and missions, or by personnel that work on the decks of aircraft carriers, that work on any type of sea craft or water vessel who spend significant time on the vessel's deck. Other wearers include racecar drivers sitting in openly exposed cockpits. But use of the goggle integrated system would probably require some alteration in the type of helmet that they wear. Applicability of the goggle integrated system will invariably depend on the balance of risks—for instance, considering whether visibility is more important than wearing a particular type of helmet, since if one is able to see better one is more likely to avoid an accident or other mishap. Other applications include motorcyclist (if precluded by the given helmet, the goggle integrated system may be adaptively configured or otherwise integrated into the visor assembly of a typical helmet), construction workers, and various others.

Depending on the location of the wiper blade units relative to the fields of view through the given lenses, the manner in which the lenses are turned may be variously controlled to optimize efficiency of cleaning. For example, debris would collect along perhaps an upper side of each wiper blade unit (relative to the ground surface). Reversing the direction of lens rotation may relocate residual debris which had been over top of the upper blade sides to engage the ground-facing lower side of the wiper blade units and get scraped off there. That is, lens rotation may be controlled in this example to allow gravity to help more effectively in removing the debris. Controlling lens rotation in that manner, however, may position the debris to fall into the wearer's field of view. Thus, each wiper blade unit is preferably so positioned and oriented that debris falling away from its bottom side (or away from either side, for that matter) will not unduly interfere with the given lens field of view. Care is taken in positioning the wiper blade units relative to the wearer's eye level—preferably, either above or below eye level, with ample clearance to avoid limiting field of view with collected/discarded debris.

Certain trade-offs must be made, according to the particular requirements of the intended application in defining the field of view through each lens, in positioning/orienting the blades, in controlling lens rotation, and the like. The trade-offs may be affected by various applicable factors like environmental conditions encountered during typical use of the system. For example, the tendency of debris to linger on the lens surface and/or blade may depend on its moisture content. With muddy debris, for instance, mud that is considerably either wet or dry may be less problematic than if the mud were of intermediate wetness. There may be a range in degree of wetness where the mud's consistency becomes particularly problematic, being unduly clunky and thick, and potentially conforming to system components and their interfaces just enough before hardening in place to 'gunk' them. If it were dry enough, the debris may be scraped off with relative ease; and if it were wet enough, the liquid-carried debris might readily flow off by itself. But if the debris consistency were somewhere in between, it may exhibit clayish properties and tend to have a seizing effect on the components.

Substantially straight longitudinally extended wiper blade unit configurations are illustrated in the exemplary embodiment shown. This is but illustrative, and in alternate embodiments, the blades may be configured with other shapes and contours suitable for the intended application. One or both blades may be formed with a curved shape/profile, for instance. Instead of a generally beam-like contour, one or both of the blades may actually be formed with slightly more material mass in certain places along their lengths, so as to define a curved contour to realize particular debris deflecting or collecting advantages. Certain embodiments and/or applications may entail optimal shapes for the blades as well as for the lens surfaces and surrounding protective shell/housing structures to facilitate the shedding of liquid and debris from the lens fields of view. Similarly, certain blade and surrounding protective shell/housing surface portions may also be formed with features such as flow channels to further accommodate the shedding of liquid and debris from the lens fields of view. Such features may for instance aid in the efficient migration of liquid and debris, such that when a lens comes around to a blade edge with enough velocity, the liquid and debris carried thereon does not just fly off when scraped from the lens surface, but is directed radially downward before being cast off the goggle integrated system.

Referring to the speed of lens rotation, the realizable angular speed and sustaining a certain rate of rotation depends largely on the available power capacity. As available battery power generally correlates to weight, there are certain trade-offs to be made in this regard, again in accordance with the particular requirements of the intended application. The system preferably provides multiple selectable rotation speeds, with selected rpm's being determined in view of the duration for continual operation at or around such rpm.

Regarding user-selective actuation of the system, such may be effected through conventional switches provided on the goggle integrated system. When, for example, a motorcycle operator is riding through dirt and rough terrain, his/her hands are occupied with numerous tasks. It may be difficult to reach up to the goggle integrated system housing to manually flip a switch. Even if the switch is of highly simple type, which may be easily toggled on/off, the effort to manually reach the switch may pose hazards to safe vehicle operation. Various measures may be employed to alleviate such hazards. For example, a remote pull string line system may be employed to actuate the system with the user's hands remaining at the vehicle controls. A wireless, automated actuation system may be employed, where the available resources permit for a given application. Such wireless activation of the cleaning mechanism may include voice-activated measures, or any other known measures available on the vehicle controls having a wireless control/communications link to the goggle integrated system's cleaning control mechanism.

Turning more closely to system power, if the power supply were sufficient, the lens cleaning operation may be turned on to run continually. Depending on the particular embodiment and application, the operation may include a built-in periodic delay between rotations, or may be programmably set. Moreover, if the given application requires—such as in the case of a professional racer for instance who is often supported by an entourage/team of personnel—a manager or other support team member who stays in remote radio contact with the racer, could by remote radio control activate the cleaning mechanism as needed, or as the racer indicates.

There are numerous ways by which hands-free control may be implemented, depending on the embodiment and application. Other ways include incorporating a control button on the handle bars, driving wheel, or the like; a low power near field wireless connection such as BLUETOOTH may be established with the goggle integrated system controller; and the like.

Regarding the goggle integrated system's comfort and ergonomic features, suitable padding and/or other elements may be employed as needed on any component of the system. These may include not only those portions directly contacting the user, but also those portions bearing particularly on overall weight and balance, or on those portions subject to regular user handling or manipulation—on which portions measures may be taken to optimize comfort and ergonomics, like applying or removing weight, and shaping, contouring, or applying attachments for convenient handling.

If the goggle integrated system is to be worn on a user's bare head, supplemental measures in addition to the strap and nose bridge combination may be employed to reinforce and stabilize its support when worn. Such mechanical features as temple-line ear-engaging members may be employed in certain embodiments. In certain other embodiments, the goggle integrated system may be incorporated with or attached to a helmet. Suitable measures are taken in view of the requirements of the intended application to keep the overall weight of the goggle integrated system within reasonably tolerable ranges.

In other applications, the goggle integrated system may be strapped to headwear other than a hard helmet. For example, the goggle integrated system may be coupled to a skull cap portion which supplements the support and hold provided by an elastic strap band by resting on the wearer's head and providing a stable top-down support member from which to suspend intermediate portions of the strap and/or goggle housing/body. Depending on the intended application, such skull cap portion may be formed with a skeletal structure, in that it may not be fully enclosed by a sheet-like surface(s), but have instead a plurality of flexible frame members joined together to 'cup' the top portion of the wearer's head in conformed manner.

The goggle housing/body and other portions of the goggle integrated system holding the lenses and electrical/mechanical components may be formed by molded plastic or any other suitable material known in the art having the combination of strength, weight, economy, durability, and the like required for the intended application.

The descriptions herein are intended to illustrate possible implementations of the present invention and are not restrictive. Although this invention has been described in connection with specific forms and embodiments thereof, it will be appreciated that various modifications other than those discussed above may be resorted to without departing from the spirit or scope of the invention as defined by the appended claims. For example, functionally equivalent elements or processes may be substituted for those specifically shown and described, certain features may be used independently of other features, and in certain cases, and particular locations of the elements or processes may be reversed or interposed, all without departing from the spirit or scope of the invention as defined by the appended claims.

What is claimed is:

1. A self-cleaning system for a vision protective lens comprising:
a chassis configured to be worn on a user's head, said chassis having a main body portion defining a field of view;
at least one lens coupled in angularly displaceable manner for rotation relative to said chassis, said lens being disposed to extend at least partially across the field of view;
at least one wiper blade unit supported on said chassis to extend across an outer surface of said lens about the field of view, said wiper blade unit including a blade portion engaging said outer surface of said lens;
at least one slew ring bearing coupled to said main body of said chassis, said slew ring bearing including a movable bearing portion coupled in angularly displaceable manner to a stationary bearing portion, said movable bearing portion supporting said lens; and,
a drive portion coupled to selectively drive angular displacement of said lens;
wherein said lens is angularly displaced responsive to said drive portion in selectively driven manner relative to said wiper blade unit, said outer surface of said lens being at least partially wiped by said blade portion of said wiper unit to be cleared prior to advancement angularly into the field of view;
wherein said drive portion engages said movable bearing portion of said slew ring bearing to drive angular displacement thereof, said drive portion including a motor and a drive gear rotationally driven thereby.

2. The system as recited in claim 1, wherein said wiper blade unit is fixedly supported on said chassis to extend radially from a central region of said lens with a downwardly inclined orientation.

3. The system as recited in claim 2, wherein said wiper blade unit includes a longitudinally extended protective shell portion and a longitudinally extended blade portion coupled thereto, said blade portion emerging transversely from said protective shell portion to engage said outer surface of said lens, said protective shell portion extending laterally beyond said blade portion to define a deflective overhang therefor.

4. The system as recited in claim 1, wherein said stationary bearing portion includes first and second inner ring members, and said movable bearing portion includes an outer ring member coaxially captured in slidable manner by said first and second inner ring members, said outer ring member having an external toothed surface circumferentially extending thereabout for meshed engagement with said drive gear.

5. The system as recited in claim 1, wherein said slew ring bearing includes a gliding interface extending between said stationary and movable bearing portions, said gliding interface defining a meandering sectional contour having a plurality of bends between a back surface of the lens and said main body portion of said chassis.

6. The system as recited in claim 5, wherein said gliding interface includes a sliding element captured between said stationary and movable bearing portions, said sliding element being formed of a plastic-based solid material having friction mitigating properties.

7. The system as recited in claim 1, wherein:
a pair of said slew ring bearings are coupled to said main body to support a pair of said lenses in angularly displaceable manner to respectively extend at least partially across the fields of view for right and left eyes of the user;
a pair of said wiper blade units are supported on said chassis to extend across respective outer surfaces of said lenses adjacent the fields of view corresponding thereto; and,
a pair of drive portions engaging respective movable bearing portions of said slew ring bearings to drive angular displacement thereof.

8. A self-cleaning system for a vision protective lens comprising:
a chassis configured to be worn on a user's head, said chassis having a main body portion defining a field of view;
at least one slew ring bearing coupled to said main body of said chassis, said slew ring bearing including a movable bearing portion coupled in angularly displaceable manner to a stationary bearing portion;
at least one lens coupled to said movable portion of said slew ring bearing for angular displacement therewith to rotate relative to said chassis, said lens being supported by said movable portion to extend at least partially across the field of view;
at least one wiper blade unit fixedly supported on said chassis to extend in inclined manner across an outer surface of said lens adjacent the field of view, said wiper blade unit including a protective shell portion and a blade portion emerging therefrom to engage said outer surface of said lens; and,
a drive portion coupled to said chassis, said drive portion engaging said slew ring bearing to selectively drive angular displacement of said movable portion thereof;
wherein said lens is angularly displaced responsive to said drive portion in selectively driven manner relative to said wiper blade unit, said outer surface of said lens being at least partially wiped by said blade portion of said wiper unit to be cleared prior to advancement angularly into the field of view;
wherein:
said drive portion includes a motor and a drive gear rotationally driven thereby; and,
said stationary bearing portion includes first and second inner ring members, and said movable bearing portion includes an outer ring member coaxially captured in slidable manner by said first and second inner ring members, said outer ring member having an external toothed surface circumferentially extending thereabout for meshed engagement with said drive gear.

9. The system as recited in claim 8, wherein said wiper blade unit includes a longitudinally extended protective shell portion and a longitudinally extended blade portion coupled thereto, said blade portion emerging transversely from said protective shell portion to engage said outer surface of said lens, said protective shell portion extending laterally beyond said blade portion to define a deflective overhang therefor.

10. The system as recited in claim 8, wherein said slew ring bearing includes a gliding interface extending between said stationary and movable bearing portions, said gliding interface defining a meandering sectional contour having a plurality of bends between a back surface of the lens and said main body portion of said chassis.

11. The system as recited in claim 10, wherein said gliding interface includes a sliding element captured between said stationary and movable bearing portions, said sliding element being formed of a plastic-based solid material having friction mitigating properties.

12. The system as recited in claim 8, wherein:
a pair of said slew ring bearings are coupled to said main body to support a pair of said lenses in angularly displaceable manner to respectively extend at least partially across the fields of view for right and left eyes of the user;
a pair of said wiper blade units are fixedly supported on said chassis to extend across respective outer surfaces of said lenses adjacent the fields of view corresponding thereto; and,
a pair of drive portions engage respective movable bearing portions of said slew ring bearings to drive angular displacement thereof.

13. The system as recited in claim 12, wherein:
each said drive portion includes a motor and a drive gear rotationally driven thereby; and,
said chassis includes a pair of side wing portions projecting from said main body portion, each said side wing portion having said motor of one said drive portion mounted thereto.

14. A self-cleaning system for a vision protective lens integrated in a goggle device comprising:
a chassis configured to be worn on a user's head, said chassis having a main body portion defining fields of view for right and left lens openings;
a pair of slew ring bearings coupled to said main body of said chassis respectively at said right and left openings, each said slew ring bearing including a movable bearing portion coupled in angularly displaceable manner to a stationary bearing portion;
a pair of lenses each coupled to said movable portion of one said slew ring bearing for angular displacement therewith to rotate relative to said chassis, said lenses being supported by said movable portions to extend over said right and left lens openings and thereby extend at least partially across the respective fields of view;
a pair of wiper blade units each fixedly supported on said chassis to extend in inclined manner across an outer surface of one of said lenses adjacent the field of view corresponding thereto, each said wiper blade unit including a protective shell portion and a blade portion emerging therefrom to engage said outer surface of one said lens; and,
a pair of drive portions coupled to said chassis, each said drive portion engaging one of said slew ring bearings to selectively drive angular displacement of said movable portion thereof, each said drive portion including a motor actuated drive gear;
wherein said lenses are angularly displaced responsive to said drive portions in selectively driven manner relative to said wiper blade units, said outer surface of each said lens being at least partially wiped by said blade portion of one said wiper unit to be cleared prior to advancement angularly into the field of view corresponding thereto.

15. The system as recited in claim 14, wherein each said wiper blade unit includes a longitudinally extended protective shell portion and a longitudinally extended blade portion coupled thereto, said blade portion emerging transversely from said protective shell portion to engage said outer surface of one said lens, said protective shell portion extending laterally beyond said blade portion to define a deflective overhang therefor.

16. The system as recited in claim 15, wherein each said stationary bearing portion includes first and second inner ring members, and said movable bearing portion includes an outer ring member coaxially captured in slidable manner by said first and second inner ring members, said outer ring member having an external toothed surface circumferentially extending thereabout for meshed engagement with said drive gear.

17. The system as recited in claim 16, wherein:
each said slew ring bearing includes a gliding interface extending between said stationary and movable bearing portions, said gliding interface defining a meandering sectional contour having a plurality of bends between a back surface of the lens and said main body portion of said chassis; and,
said gliding interface includes a sliding element captured between said stationary and movable bearing portions, said sliding element being formed of a plastic-based solid material having friction mitigating properties.

* * * * *